United States Patent [19]

Cully

[11] Plant 4,409

[45] Apr. 24, 1979

[54] BIRCH TREE

[76] Inventor: Earl Cully, R.R. #5, Jacksonville, Ill. 62650

[21] Appl. No.: 875,381

[22] Filed: Feb. 6, 1978

[51] Int. Cl.[2] ..... A01H 5/12
[52] U.S. Cl. ..... Plt./51
[58] Field of Search ..... Plt./51

*Primary Examiner*—Robert E. Bagwill
*Attorney, Agent, or Firm*—William A. Snow

[57] ABSTRACT

This disclosure concerns a new and distinct variety of a new cultivar of *Betula nigra,* characterized by its rapid growth, dense branching habit, large dark green leaves and the varying color of the bark during the year depending on the amount of exfoliation taking place, starting with a grayish brown bark and transitional stages during exfoliation from light tan to creamy white to white, with flaking in large sheets.

6 Drawing Figures

BACKGROUND OF THE INVENTION

This new variety of birch tree was discovered by me in St. Louis, Mo., on cultivated property. During the past several years, I have grafted cuttings from this parent tree at Cully Nursery in Jacksonville, Ill., on river birch seedlings (*B. nigra*) and canoe birch seedlings (*B. papyrifera*). I have also rooted it from soft wood cuttings taken in June under mist. At the present time, I have several thousand grafts growing true to form and they are rapid growers.

Figure 1:
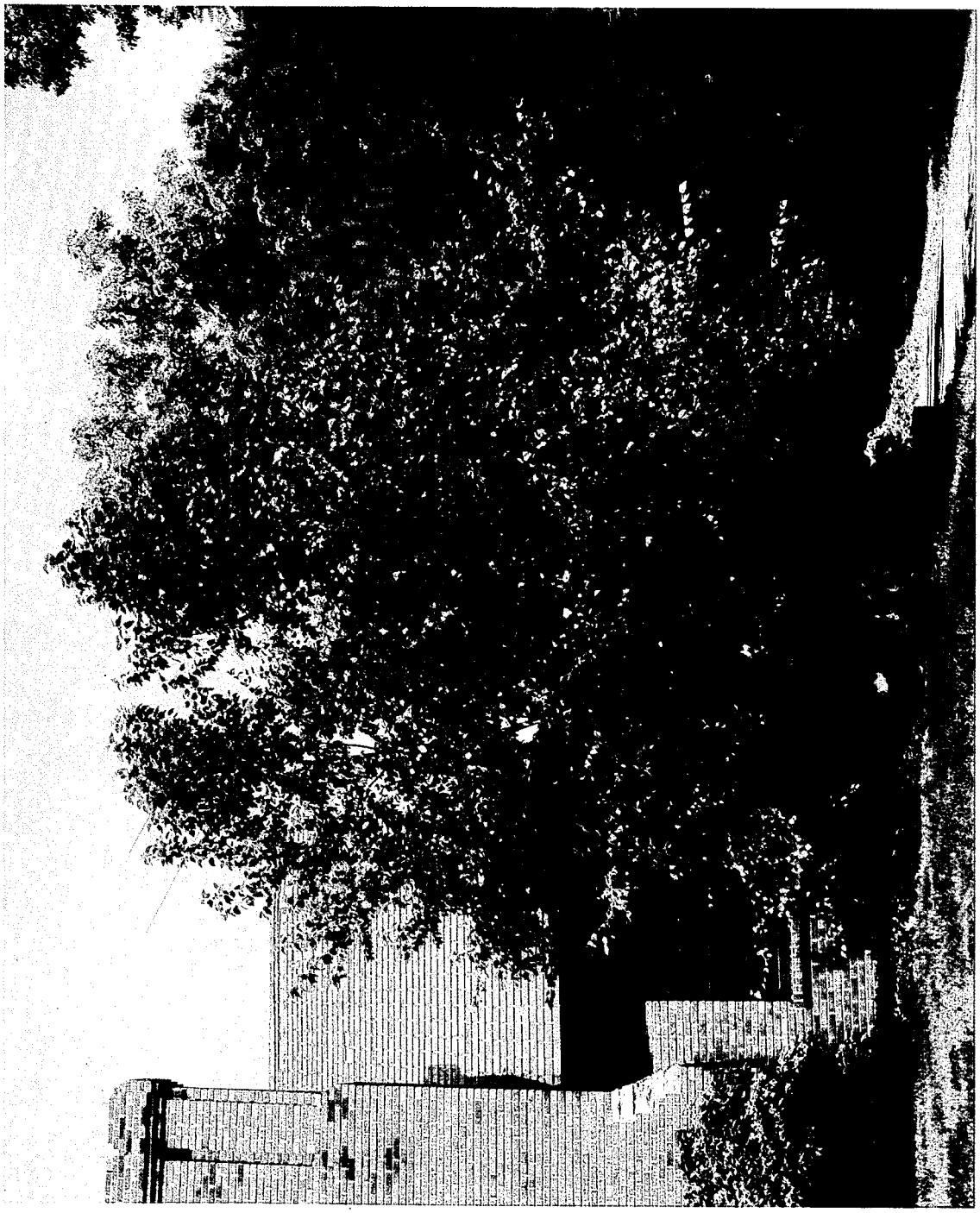
FIG. 1 is a photograph of the parent tree approximately twelve years old.
Figure 2:
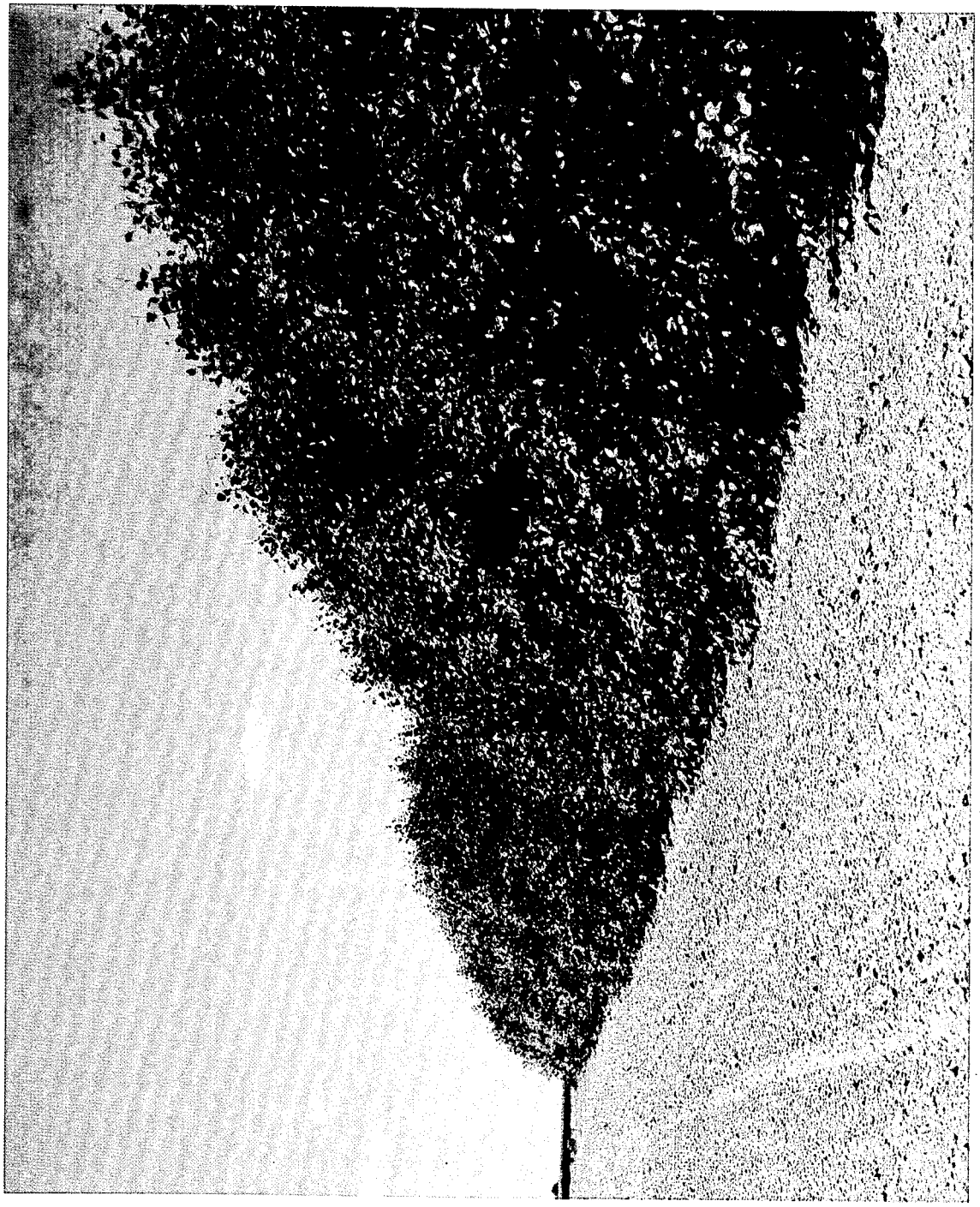
FIG. 2 is a photograph of a row of stock plants at Cully Nursery at the age of four years.
Figure 3:
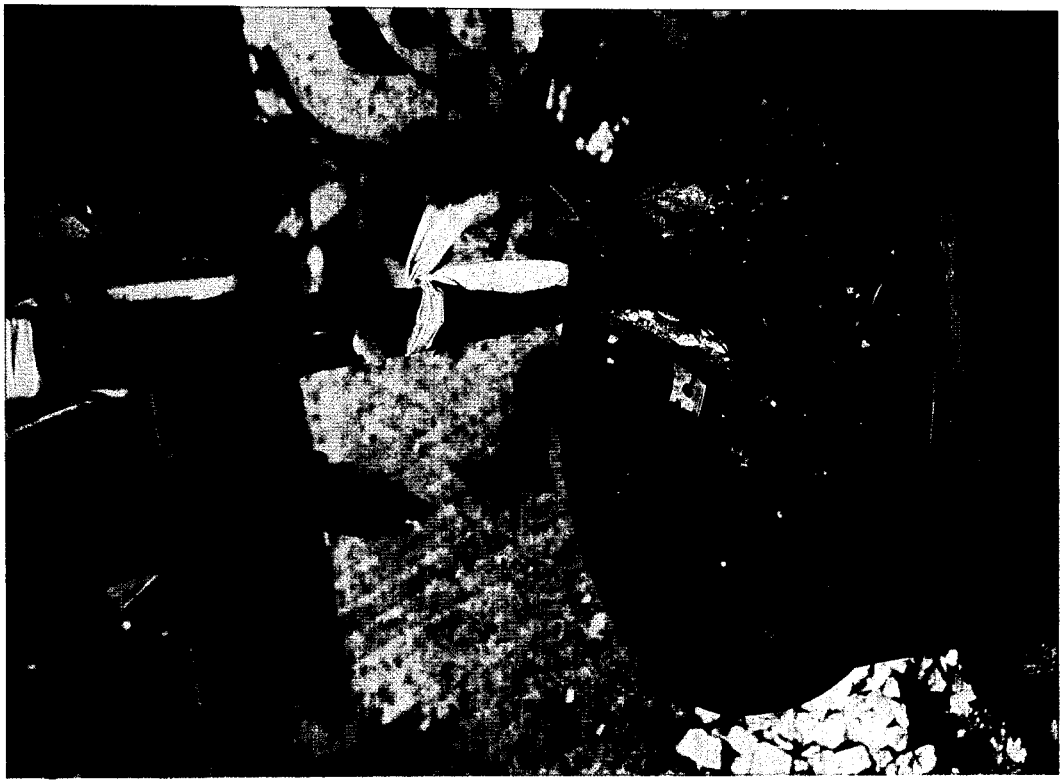
FIG. 3 is a photograph of a three months old graft.
Figure 4:
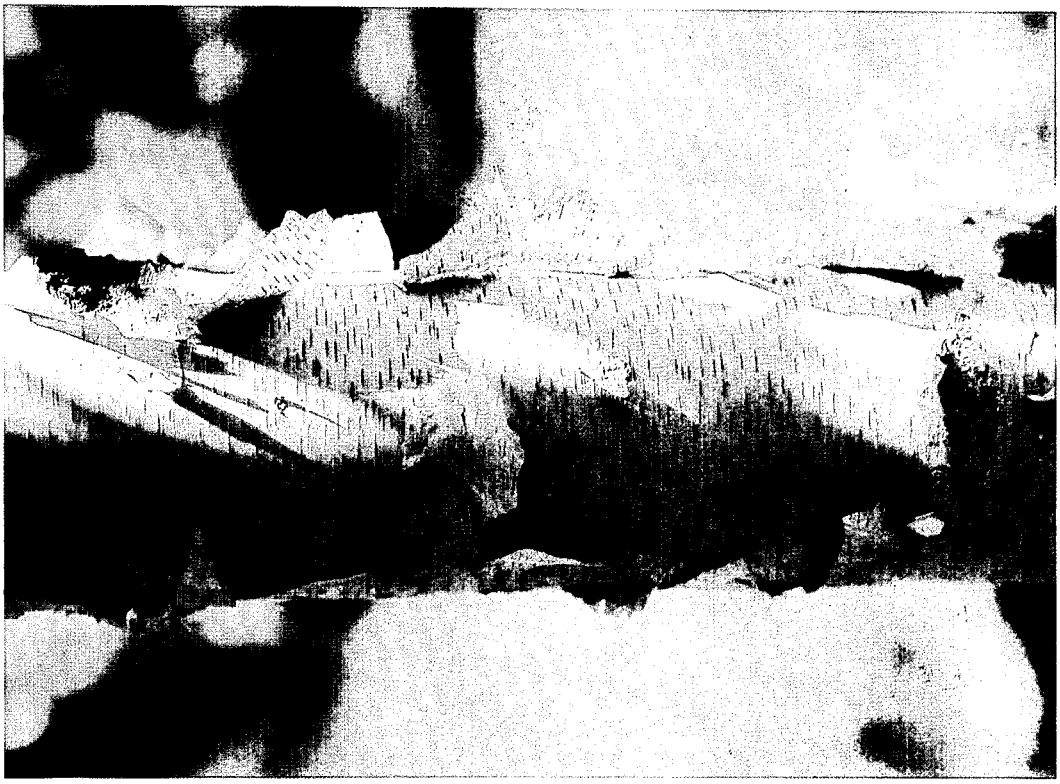
FIG. 4 is a photograph showing the bark of a grafted hybrid birch tree taken about six feet from the ground.
Figure 6:
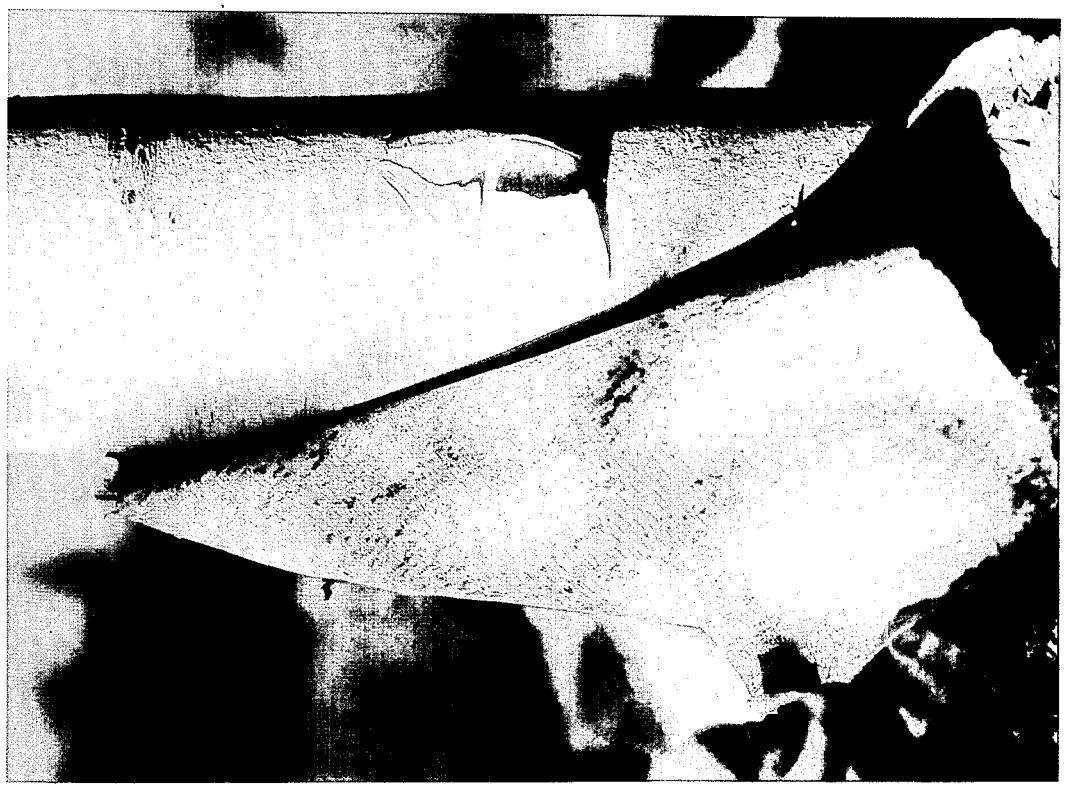
FIG. 6 is a photograph showing the trunk of the grafted hybrid taken about two feet from the ground and showing large exfoliating sheets of bark.
Figure 5:
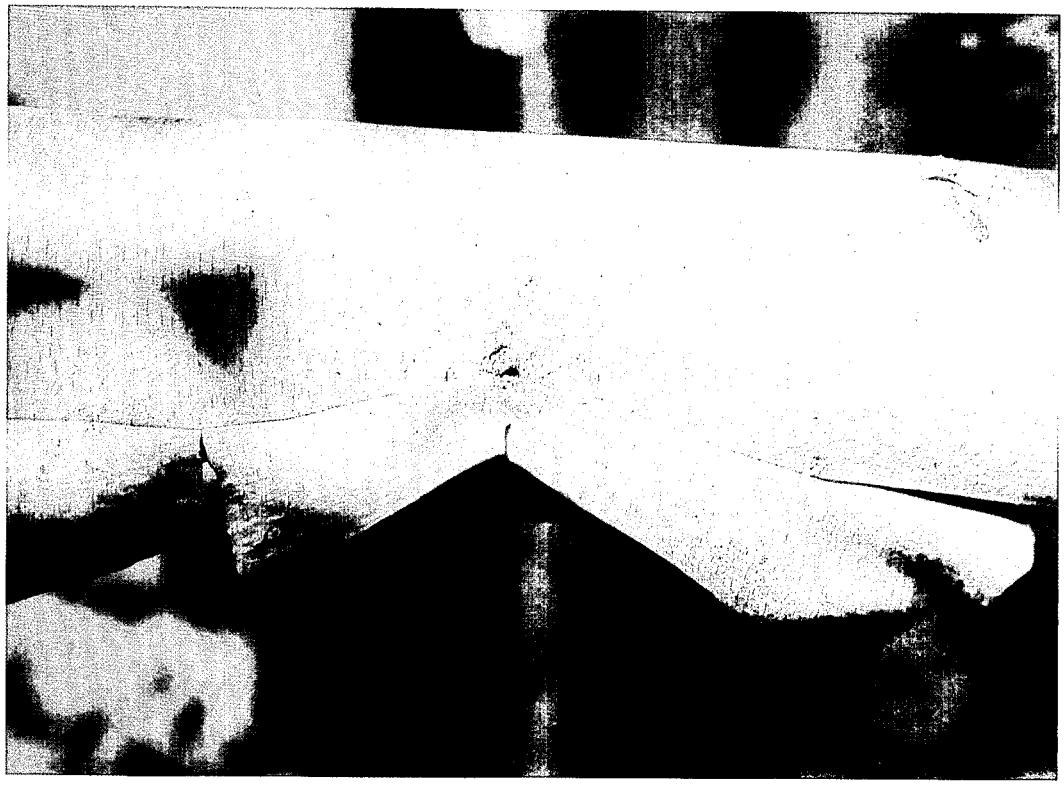
FIG. 5 is a photograph showing a closeup of the bark taken in June or July of a six year old graft of this new variety.

The colors shown are as nearly true as it is reasonably possible to obtain by conventional photographic procedures.

DESCRIPTION OF THE NEW PLANT

The following is a detailed description of my new hybrid birch tree with color designations according to The R.H.S. Colour Chart published by The Royal Horticultural Society of London, England, the stated observations having been made of trees growing at Jacksonville, Ill.

Origin: Seedling.
Parentage: Unknown.
Classification: *Betula nigra.*
Form: Tree.
Shape: Pyramidal; oval; rounded.
Height: 30 feet.
Trunk Size: Multi-stemmed $3\frac{1}{2}''$, $3\frac{3}{8}''$ and $3\frac{3}{4}''$.
Growth Rate: Rapid for its species.

Bark: Grayish brown to tan to creamy white to white during the year.
Exfoliation: During the growing season in substantially large sheets.
Branches:
- *Angle of attachment.*—From 45° to 60°.
- *Spacing.*—Regular.
- *Size.*—1 inch.
- *Bark.*—Shades of grayish brown to tan to creamy white to white, 159A, 159B, 159C, 155A and 158A.

Lenticels:
- *Size.*—1 to 2 cm.
- *Quantity.*—Numerous.
- *Color.*—Orange brown 165B.

Leaves:
- *Length.*—9–13 cm.
- *Width.*—8–10 cm.
- *Form.*—Ovate.
- *Margin type.*—Dentate, each dentate showing 2 to 5 smaller serrations.
- *Texture.*—Leathery and glossy; smooth and glabrous.
- *Pubescence distribution.*—On lower side of leaf.
- *Quantity.*—Abundant.
- *Color.*—Upper side — Dark green 147A. Lower side — Gray green 148A.
- *Petioles.*—Length — 1 to 2 cm.
- *Ribs and veins.*—6 to 11.
- *Thorns, spines and prickles.*—None.

This new variety most resembles *Betula nigra* and *Betula papyrifera* but clearly distinguishes from them by the transitional stages of the bark as to color and exfoliation, large sheets of flaking during the entire growing season, vigorous grower, dense branching habit, an oval to round growth habit, the branches being stout.

I claim:

1. A new and distinct variety of birch tree substantially as herein shown and described, characterized by its rapid growth habit, its transitional stages of bark as to color and exfoliation continuously during the growing season with large sheets of flaking, the outer bark coloration being brown to tan and the inner bark creamy white to white, the larger size of the dark green leaves, the dense branching, and its ability to withstand wind and ice breakage.

* * * * *